United States Patent
Gutierrez

(12) 
(10) Patent No.: US 7,147,622 B2
(45) Date of Patent: ***Dec. 12, 2006

(54) I.V. CATHETER ASSEMBLY WITH BLOOD EXPOSURE PREVENTION

(76) Inventor: Raymond Gutierrez, 1816 Tall Ships Ct., Toms River, NJ (US) 08755

( * ) Notice: Subject to any disclaimer, the term of this patent is extended or adjusted under 35 U.S.C. 154(b) by 148 days.

This patent is subject to a terminal disclaimer.

(21) Appl. No.: 10/849,722

(22) Filed: May 20, 2004

(65) Prior Publication Data

US 2004/0215145 A1    Oct. 28, 2004

Related U.S. Application Data

(63) Continuation of application No. 10/300,394, filed on Nov. 20, 2002, now Pat. No. 6,814,725.

(51) Int. Cl.
*A61M 5/178*     (2006.01)

(52) U.S. Cl. .............................. 604/164.01; 604/164.08

(58) Field of Classification Search ............ 604/164.01, 604/508, 187, 264, 272, 93.01
See application file for complete search history.

(56) References Cited

U.S. PATENT DOCUMENTS 6,814,725 B1 *  11/2004  Gutierrez ..................... 604/508

* cited by examiner

*Primary Examiner*—Catherine S. Williams
(74) *Attorney, Agent, or Firm*—Notaro & Michalos PC

(57) ABSTRACT

I.V. catheter assembly was a catheter with a distal needle for insertion into a blood vessel a portion of the catheter. An adapter with a self-sealing or self-closing plug is connected to the catheter, proximally of the distal needle. A proximal needle that can couple to the distal needle is in a guard tube on the other side of the plug. In use the proximal needle is pushed through the plug and into coupling engagement with the distal needle so the distal needle can be inserted into a blood vessel. The coupled needles are then withdrawn and shielded in the guard tube. The guard tube is then disconnected from the adapter and the adapter can be used to discharge blood from, or supply fluid to the blood vessel.

9 Claims, 3 Drawing Sheets

I.V. CATHETER ASSEMBLY WITH BLOOD EXPOSURE PREVENTION

CROSS-REFERENCE TO RELATED APPLICATION

This is a continuation of application Ser. No. 10/300,394, filed Nov. 20, 2002, now U.S. Pat. No. 6,814,725.

FIELD AND BACKGROUND OF THE INVENTION

The present invention relates in general, to intravascular (I.V.) catheter assemblies, and in particular, to a new and useful I.V. catheter assembly that prevents blood from accidentally leaking from the catheter.

A typical I.V. catheter assembly requires the user to remove and then dispose of a contaminated needle after the needle tip and the catheter are properly located in a blood vessel of a patient. Once the needle is withdrawn from the catheter, the user immediately discards the needle. The user then urgently attempts to attach a male adapter to the catheter. The adapter can be of various types but almost always has a self-closing plug or member into or through which the needle of a supply tube or a needless system can be passed for drawing blood from the patient or for supplying appropriate fluids to the patient.

The user is trying to prevent the patients' blood from accidentally leaking out of the catheter hub and onto the user, the patient, the bed and/or the floor. Once the male adapter is attached to the catheter hub, the user then has time to secure the catheter and draw blood and/or provide the patient with I.V. fluids.

The main concern during this entire attachment sequence which starts with injection of the catheter and needle into the patients blood vessel, and ends with the attachment of a fluid receiving or supplying tube to the adapter, is protecting the user, the patient and everyone else involved, against exposure to blood borne pathogens such as hepatitis and HIV/AIDS. Often, typical I.V. catheter assemblies come with some sort of needle guard to help prevent accidental self-inflicted needle injuries. Unfortunately they do not efficiently prevent blood from leaking out of the catheter prior to attachment of the adaptor.

See for example, U.S. Pat. No. 5,000,740 to Ducharme et al. which is incorporated here by reference for disclosing a needle guard which covers and locks the catheter needle of the prior art when the needle has been withdrawn from the catheter. This and other catheter assemblies are sold by Ethicon. This and other catheter assemblies can be adapted for use with the present invention.

Other needle point covering means of the needle guard type are disclosed in U.S. Pat. Nos. 4,917,669 and 4,655,750. These and other needle point covering means can be adapted for use with the present invention.

Other types of needle point cover means which can also be used with the present invention include a spring cover mechanism disclosed in U.S. Pat. Nos. 6,117,108 k and 6,287,278 to Woehr et al. This and other catheter assemblies are sold by B. Braun Melsungen, A G. and can be adapted for use with the present invention.

Several types of I.V. catheters that prevent accidental blood leak have been proposed. They typically work via either a valve mechanism and/or alternative site with a stopcock device. The first type generally are either expensive, inconsistent and/or do not perform the desired function. The latter types are also expensive, inconsistent and often are cumbersome and awkward.

See, for example, U.S. Pat. No. 4,245,635 to Kontos; U.S. Pat. No. 4,512,766 to Vailancourt; U.S. Pat. No. 4,883,461 to Sawyer; U.S. Pat. No. 5,053,014 to VanHeugten; U.S. Pat. No. 5,098,396 to Taylor, et al.; U.S. Pat. No. 5,376,071 to Henderson; U.S. Pat. No. 5,954,698 to Pike; U.S. Pat. No. 6,221,050 to Ishida; and U.S. Pat. No. 6,413,250 to Smith; and U.S. Pat. No. 6,322,537 to Chang.

Various other technologies have also been developed for shielding the point of a catheter needle when it is extracted from the catheter of a catheter assembly. See for example, U.S. Pat. No. 4,762,516 to Luther, et al.; U.S. Pat. No. 5,013,304 to Russell, et al.; U.S. Pat. No. 5,573,510 to Isaacson; U.S. Pat. No. 5,575,777 to Cover, et al.; U.S. Pat. No. 5,685,855 to Erskine; U.S. Pat. No. 5,695,474 to Daugherty; and U.S. Pat. No. 6,436,070 to Botich, et al. They can also be adapted for use with the present invention.

Also see U.S. Pat. No. 5,009,642 to Sahi for a self blunting needle and additional valve systems of U.S. Pat. No. 4,525,157 and U.S. Pat. No. 4,655,750 to Vaillancourt; U.S. Pat. No. 4,917,668 to Haindl; U.S. Pat. No. 5,092,845 to Chang; U.S. Pat. No. 5,156,792 to Holdaway, et al.; U.S. Pat. No. 5,405,323 to Rogers, et al.; U.S. Pat. No. 5,419,766 to Chang, et al.; and U.S. Pat. No. 5,851,196 to Arnett.

Many of these known catheter assemblies and others not yet known can benefit by use of the present invention.

SUMMARY OF THE INVENTION

In accordance with the present invention an I.V. catheter assembly has an adapter with self-closing plug member already attached to the catheter hub. The single needle of the prior art is, in effect, divided into two parts that are provided on either side of the adaptor. Just prior to its use, the user will advance the proximal or outer needle thru the plug member of the adaptor and into coupling engagement with the distal or inner needle. The distal end of the outer needle is shaped to engage and firmly couple with the proximal end of the inner needle to, in effect, form one needle again. The I.V. catheter assembly of the invention is then ready for use.

The distal needle extends through a catheter of the assembly as in the prior art, and has a distal point that is inserted in the blood vessel of the patient along with a length of the catheter. Once the catheter is in place in the patient's blood vessel, the distal needle is withdrawn from the catheter and is pulled back and out through the self-closing plug by the proximal needle which is pulled back out through the plug.

In a preferred embodiment of the invention, the distal point of the distal needle is automatically covered when the coupled needles are pulled out of the catheter for protection against inadvertently being stuck by the needle point.

The great advantage of the present invention is that the plug member never allows blood to leak from the catheter assembly during any phase of its use.

Besides the objects and advantages of a bloodless I.V. catheter, the invention has several other objects and advantages including:

Providing an I.V. catheter assembly that reliably prevents accidental blood exposure to the user, the patient, and everyone involved and/or nearby;

Providing an environment which the user, the patient, the other medical staff, the janitorial staff and the linen cleaning staff will all benefit from and appreciate;

Providing an I.V. catheter assembly that is easy to manufacture;

Providing an I.V. catheter assembly that is inexpensive and cost efficient;

Providing an I.V. catheter assembly that can be applied to other I.V. catheter assemblies that have needle guards; and Providing an I.V. catheter that is not cumbersome and/or awkward.

Accordingly, another object of the invention is to provide an I.V. catheter assembly comprised of a catheter with a distal needle therein for insertion into a blood vessel along with a portion of the catheter, an adapter with a self-sealing or self-closing plug connected to the catheter, proximally of the distal needle, a proximal needle that can couple to the distal needle in a guard tube on the proximal side of the plug, the proximal needle being movable through the plug and into coupling engagement with the distal needle so the distal needle can be inserted into a blood vessel and the coupled needles can be withdrawn into the guard tube.

The guard tube advantageously shields the coupled needles when the coupled needles are withdrawn.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
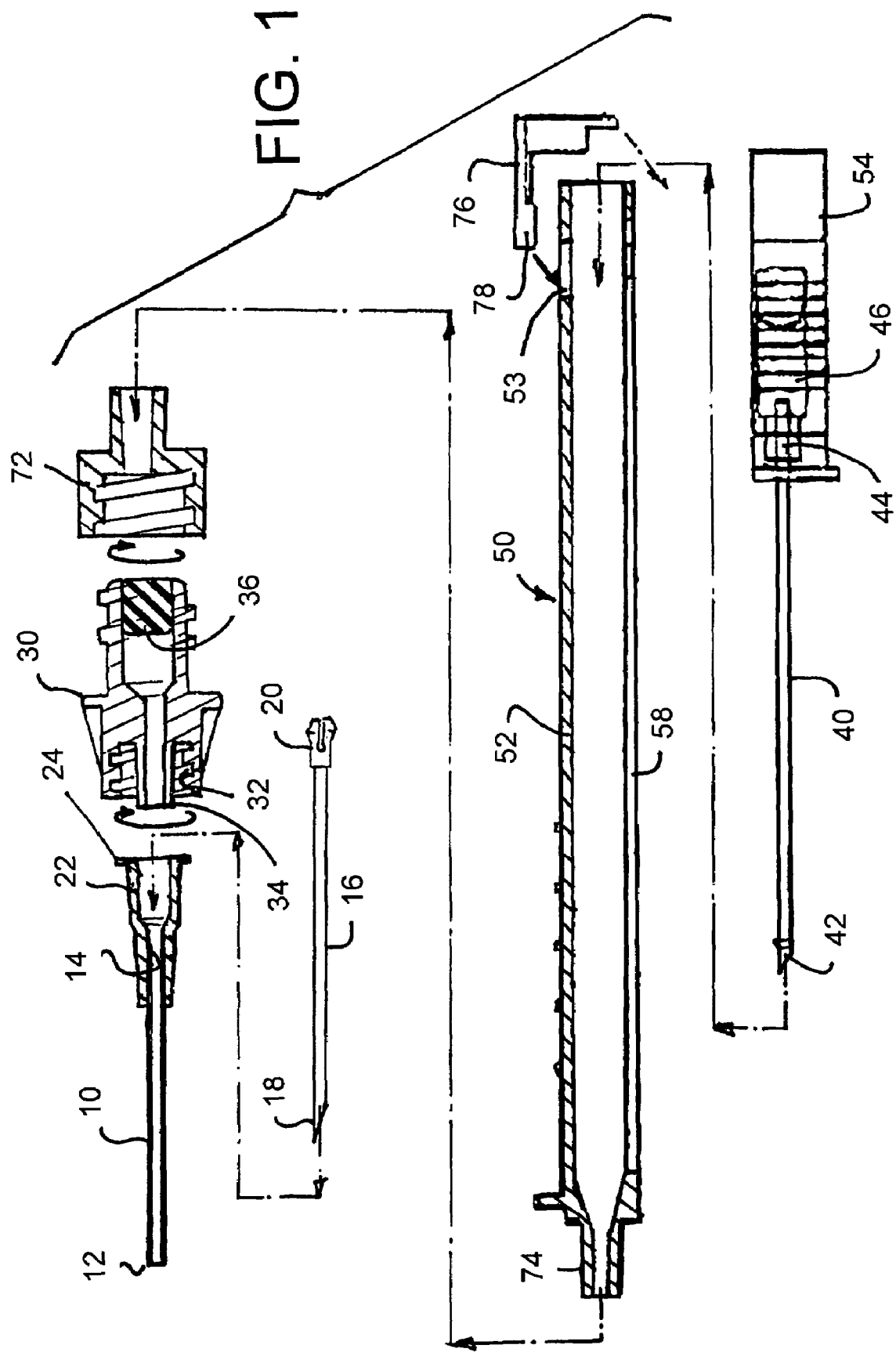
FIG. 1 is an exploded sectional view of an I.V. catheter assembly with blood exposure protection embodying my invention.

Referring now to the drawings, in which like reference numerals are used to refer to the same or similar elements, FIG. 1 illustrates an intravascular catheter assembly comprising a sterile plastic catheter 10 for insertion into a blood vessel (not shown), the catheter having a hollow lumen with an open distal end 12 and an open proximal end 14.

Figure 2:
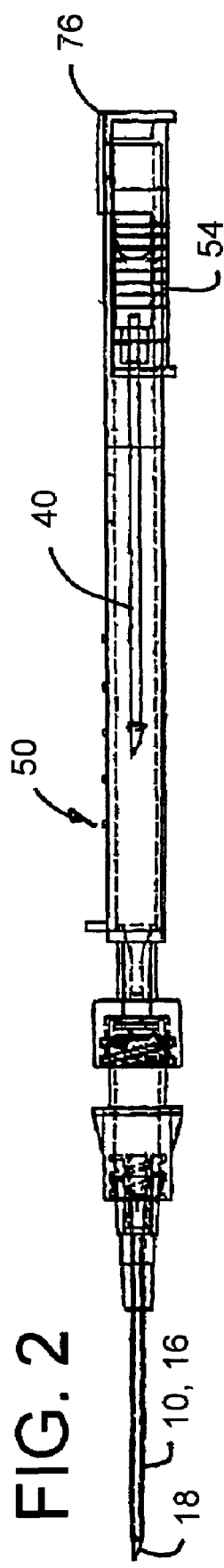
FIG. 2 is a side view thereof in an assembled state, and how it arrives in the package prior to its use.

An inner or distal needle 16 made of steel or other appropriate sterilized material extends through the catheter lumen in an injection position of the distal needle shown in FIG. 2. The distal needle 16 has a distal injection end or point 18 which extends beyond the open distal end 12 of the catheter 10 in the injection position, for insertion into a blood vessel with at least a portion of the catheter in a known fashion. The distal needle 16 also has a proximal end 20, configured to prevent forward movement beyond its FIGS. 2 and 3 position.

The distal needle 16 has means, e.g. the coupling shoulder or enlargement 20 or other enlargement, to keep it from going forward (distally) of its injection position, even when pushed by the proximal needle 40. At least part of the distal needle 16 is therefore larger in diameter than the opening at 14 in the hub 22 into which the needle extends.

A plastic catheter hub 22 is fixed to the proximal end 14 of the catheter 10 and has a helical flange 24 so that it can be threadably connected to an adapter 30 of the invention.

Although the hub 22 and adapter 30 are shown as separate parts, they can be made as one integral part within the scope of this invention.

Adapter 30 is connected to the proximal end of the catheter by threading the hub flange 24 into a threaded distal bore 32 of the adapter. A central Luer projection 34 of the adapter is tapered to press fit in a liquid-tight manner to the interior of hub 22 in a known manner. The adapter 30 has a self-sealing or self-closing plug 36 of resilient elastomer for blocking blood flow from the catheter 10.

The length of the shoulder 20 and/or the distal needle 16 is determined by the length of the chamber formed in the catheter hub 22 and the adapter 30 so that the distal needle 16 cannot move back (proximally) any further than the plug 36, with the point 18 of the distal needle still projecting from the end of catheter 10. In this way even if the distal needle accidentally moves priximally before the unit is to be used, the point 18 will remain beyond the end 12 of catheter 10 until the unit is ready for the injection process.

Adapter 30 and plug 36 are of any known or yet to be discovered type that is adapted to receive a connector such as another needle or needless device, for connecting to the adapter to discharge blood from the blood vessel or to supply fluid to the blood vessel. Examples of the adapter 30 are the self-closing slotted Baxter International Inc. adapter disclosed in U.S. Pat. No. 5,188,620 to Jepson et al., or the self-sealing (or self-healing) plug in a more common adapter where the plug can be punctured many times and self-seals each time when the needle is removed. The catheter 10/14/22 may also be of any known or yet to be discovered type.

Figure 3:
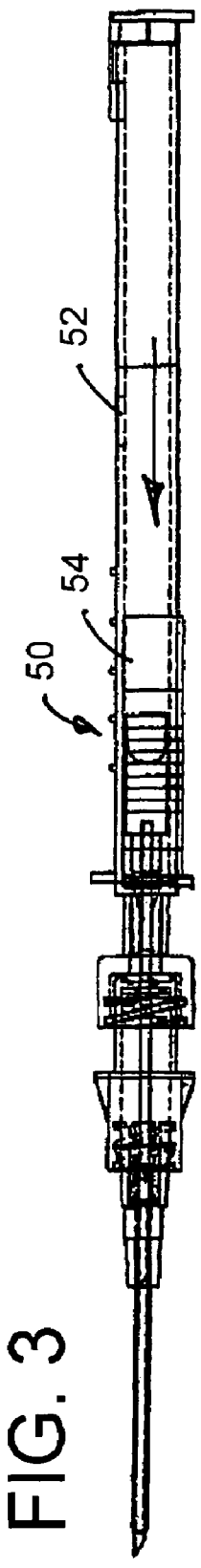
FIG. 3 is a view similar to FIG. 2, with the needles engaged in preparation for injecting the distal needle with catheter into the blood vessel of a patient in a ready-to-use state.

The distal needle 16 is distally or forwardly of the plug 36 in the injection position of the distal needle as shown in FIGS. 2 and 3.

A proximal needle 40 also of steel or other suitable material, having a distal end 42, extends toward the distal needle 16. Proximal or outer needle 40 has a proximal end 44 fixed to a cylindrical needle holder 46 extending away from the distal needle 16.

Figure 5:
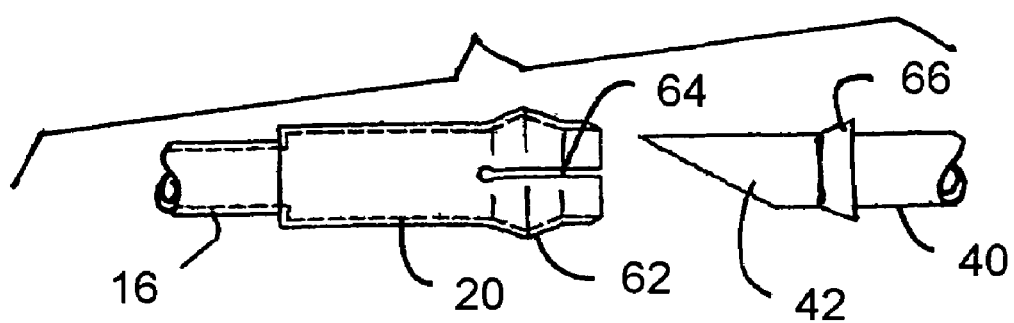
FIG. 5 is a partial exploded view on a greatly enlarged scale of the coupling arrangement between the distal end of the outer needle and the proximal end of the inner needle.
Figure 6:
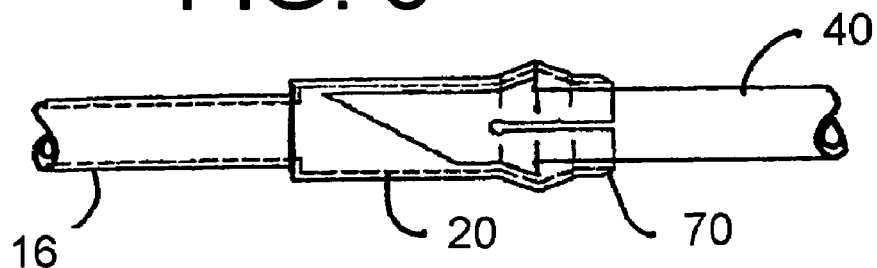
FIG. 6 is an assembled view of the coupling arrangement of FIG. 5.

Needle coupling means are engageable between the distal end 42 of the proximal needle 40 and the proximal end 20 of the distal needle 16 for coupling the needles to each other. One non-limiting example is best illustrated in FIGS. 5 and 6 which will be explained later in this disclosure.

Needle holding means 50 is detachably jointed to the adapter 30 e.g. via a jointing member 72, for holding the proximal needle 40 in a storage position proximally of the plug as shown in FIG. 2. These or any other suitable needle holding means 50 function to guide movement of the proximal needle 40 in a distal direction shown by the arrow in FIG. 3, toward the distal needle 16 for moving the distal end 42 of the proximal needle through the plug 36 and into coupling engagement with the proximal end 20 of the distal needle by action of the needle coupling means. This coupled position is shown in FIG. 3 and is an operative position for the proximal needle 40 when coupled with the distal needle 16 with the distal needle in its injection position. In this position of FIG. 3, the distal needle 16 can be injected into a blood vessel along with a portion of the catheter in a known manner.

Figure 4:
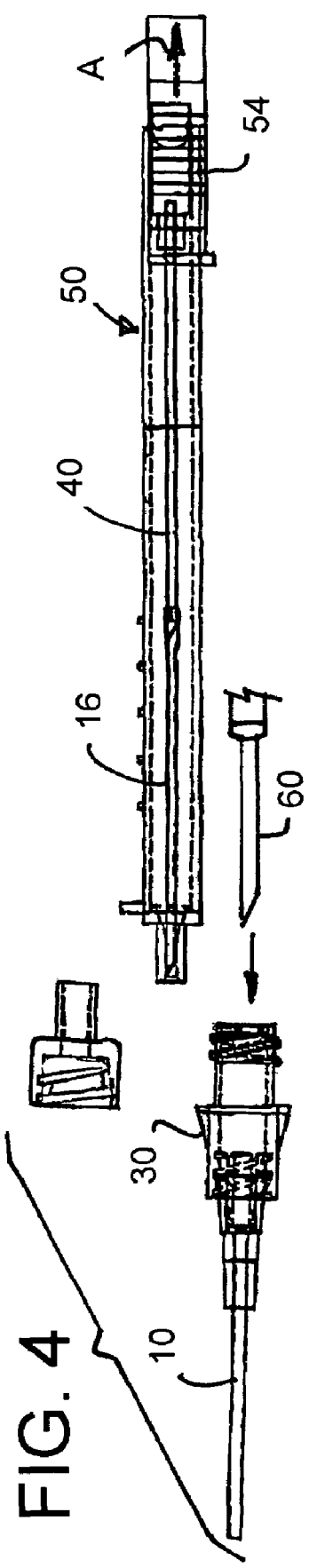
FIG. 4 is an exploded side view of the assembly with the needles withdrawn to a safe position in the needle guard and the adaptor of the invention exposed for receiving the connector of a fluid supplying or blood collecting arrangement.

Once in place in the blood vessel the distal needle 16 is withdrawn from the catheter 10 by being pulled back in the proximal direction of arrow A in FIG. 4. This is the withdrawn position for the needles which leaves the catheter 10 in place in the blood vessel and pulls the distal needle from the catheter 10 and through the plug 36. With both needles in the needle holding means 50, the needle holding means can be disconnected from the adapter 30 for the purpose of exposing the adapter for connection to a connector, e.g. a further needle 60, or needless connector, for drawing blood from the catheter 10 or for connecting a fluid supply for the blood vessel.

In a preferred embodiment of the invention, the assembly includes needle point shielding means 74 for shielding the distal point 18 of the distal needle 16 when the coupled needles 16, 40 are in the withdrawn position.

Figure 7:
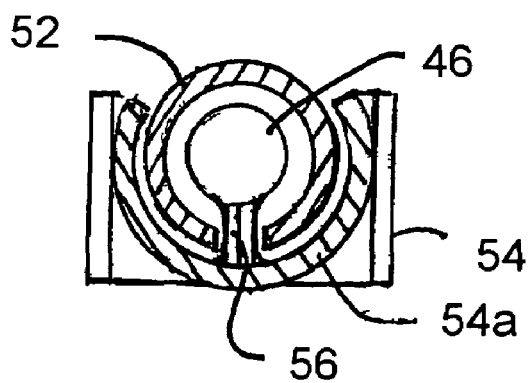
FIG. 7 is a rear elevational view of the needle guard and outer needle holder illustrating the relationship between these parts of the FIG. 1 embodiment.

In FIG. 1, the needle point shielding means 74 is part of the needle holding means 50, since both include a needle guard tube 52 of clear plastic which is of sufficient length to enclose the full length of the coupled needles (FIG. 4) when the needles have been pulled back to the withdrawn position by a needle handle 54. As best shown in FIG. 7, the needle handle 54 is C-shaped in cross-section and embraces the lower part of the guard tube 52. The needle holder 46 that is fixed to the proximal end 44 of needle 40, is connected to the needle handle 54 by a radially extending post 56 that slides in a longitudinal slot 58 of the guard tube 52 so that the needle handle 54 and needle 40 can slide from the storage position of FIG. 2, to the operative position of FIG. 3 and then to the withdrawn position of FIG. 4.

Figure 8:
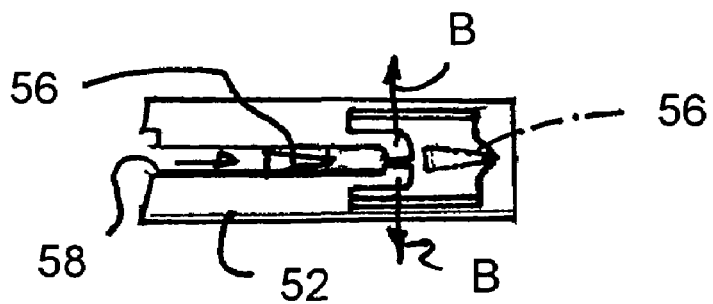
FIG. 8 is a partial bottom view of the needle guard illustrating a locking mechanism of the embodiment shown.

In FIG. 8 the withdrawn position the post 56, which is triangular in cross-section with a point toward the proximal direction, spreads two resilient fingers formed at the proximal end of slot 58 in the direction of arrows B, and passes into a trap shown as a phantom-line position of the post 56 at the proximal end of tube 52. This is like the needle cover of U.S. Pat. No. 5,000,740, but designed to accommodate both needles 16 and 40.

FIGS. 5 and 6 illustrate an embodiment of the needle coupling means. In these figures, the proximal end 20 of needle 16 has an enlargement with an annular extension 62 and one or more stress relief slots 64 to receive the distal end 42 of needle 40 which includes an annular locking ring 66 that can engaged into the extension 62 in the distal direction but is locked to needle 16 in the proximal direction. This is the coupled position of FIG. 6 which is strong enough to pull needle 16 proximally through the plug 36. To help this passage and avoid damage to the adapter plug which must remain operable for other needle-like or needless connectors, and which must maintain the blood seal to avoid leakage of blood from catheter 10, the proximal edge 70 of the needle enlargement is beveled or tapered.

Referring back to FIG. 1, the needle guard tube 52 is detachably jointed to the adapter 30 by a jointing member 72 having a female threaded end for threading onto a male thread of the adapter 30, and an opposite end with a tapered bore for receiving, in a press-fit liquid tight manner, a tapered, distal projection 74 of tube 52. The joining member 72 ensures proper alignment of the two needles. The jointing member 72 is removed after its initial use.

To prevent accidental premature locking of the needles, the proximal end of the tube 52 is covered by a housing lock 76 held by a tab 78 in a top slot 53 of the tube 50. This lock 76 is popped off by pulling on the tab 78. The lock 76 is discarded when readying the I.V. catheter for use. In FIG. 2 lock 76 holds the needle handle 54 in the rearward (proximal) position.

While a specific embodiment of the invention has been shown and described in detail to illustrate the application of the principles of the invention, it will be understood that the invention may be embodied otherwise without departing from such principles.

What is claimed is:

1. An I.V. catheter assembly comprising: a catheter; a first distal needle in the catheter, the first distal needle being adapted for insertion into a blood vessel together with a portion of the catheter; an adapter having a self-sealing or self-closing plug, the adapter being connected to the catheter; a second proximal needle that is adapted to be coupled to the first distal needle; a needle holding means for holding the second proximal needle on a proximal side of the first distal needle; the second proximal needle being movable through the plug and into coupling engagement with the first distal needle to form coupled needles which move together so the first distal needle is inserted into a blood vessel and the coupled needles are then adapted to be withdrawn together proximally from the catheter.

2. An assembly according to claim 1, wherein the needle holding means comprises a guard tube into which the withdrawn coupled needles are moved to shield the coupled needles when the coupled needles are withdrawn, and a needle handle connected to the second proximal needle and movable along the guard tube.

3. An assembly according to claim 1, including needle point shielding means for shielding a distal point of the first distal needle when the coupled needles are in the withdrawn position.

4. An assembly according to claim 1, including a catheter hub fixed to a proximal end of the catheter and connected to the adapter.

5. An assembly according to claim 4, wherein the catheter hub is removably connected to the adapter.

6. An assembly according to claim 1, wherein the needle holding means comprises a needle guard tube for accommodating distal and proximal movement of the second proximal needle, the guard tube being detachably joined to the adapter.

7. An assembly according to claim 1, wherein the adapter plug is made of self-sealing elastomer.

8. An assembly according to claim 1, wherein the needle holding means comprises a guard tube and a needle handle movable in distal and proximal directions in the guard tube, locking means for locking the coupled needles in a withdrawn position in the guard tube and the guard tube covering the distal end of the first distal needle in the withdrawn position for shielding the distal end of the first distal needle.

9. An assembly according to claim 8, including a lock at a proximal end of the guard tube for holding the needle handle in the storage position.

* * * * *